United States Patent [19]
Abramson et al.

[11] Patent Number: 5,824,294
[45] Date of Patent: Oct. 20, 1998

[54] SAND REMOVING BODY POWDER

[76] Inventors: Trevor David Abramson; Adele Abramson, both of 2055 Holmby Ave., Los Angeles, Calif. 90025

[21] Appl. No.: 950,689

[22] Filed: Oct. 15, 1997

[51] Int. Cl.$^6$ .......................... A61K 7/035; A61K 33/42; A61K 33/00; A61K 47/00
[52] U.S. Cl. ............................ 424/69; 424/602; 424/717; 514/778
[58] Field of Search ............................ 424/69, 602, 717; 514/778

[56] References Cited

U.S. PATENT DOCUMENTS 4,568,539  2/1986  Ashton et al. .
4,913,896  4/1990  Harvey .

OTHER PUBLICATIONS

Dialog File 16 abstract 03306148 "Shower to Shower Deodorant Body Powder–Spring Fresh Scent", Aug. 1991.
Physicians' Desk Reference for Non–Prescription Drugs, 6th ed. p. 697, 1985.
Handbook of Nonprescription Drugs, 8th edition, p. 652, 1986.
Handbook of Pharmaceutical Excipients, pp. 34–35, 1986.

*Primary Examiner*—Raymond Henley, III
*Attorney, Agent, or Firm*—Sonnenschein Nath & Rosenthal

[57] ABSTRACT

A body powder composition useful for removing sand adhered to a user's body. The composition comprises a major amount of cornstarch. A related method for removing sand off the body is also disclosed comprising the steps of liberally applying a powder composition containing a major amount of cornstarch to an area of the body having sand adhered thereto; rubbing said composition on said area; and wiping said composition and said sand off the area using one's hands or a towel or the like.

8 Claims, No Drawings

SAND REMOVING BODY POWDER

FIELD OF THE INVENTION

The present invention relates to body powder compositions and, more particularly, to a cornstarch body powder composition useful in removing sand from the skin.

BACKGROUND OF THE INVENTION

Body powders have long been available to the consuming public, primarily for absorbing moisture and body oils from the sebaceous and sweat glands. Body powders have also been used extensively on babies to help prevent diaper rash and to otherwise help maintain dryness. None of such prior art body powders have been utilized for the specific purpose of removing sand from the body. Beachcombers have long dealt with the problem of sand adhering to their bodies, especially their legs and feet, after swimming or sunbathing. Sand on the feet makes it difficult and uncomfortable to wear shoes or sandals. It would therefore be an advantage in the art if there was a body powder composition which could be used upon leaving the beach to easily remove sand, allowing one to get dressed on the beach, without having to immediately shower.

SUMMARY OF THE INVENTION

It is an object of this invention to provide improved body powder compositions to remove sand from the body.

It is another object of this invention to provide body powder compositions to remove sand having improved moisture absorbency and aesthetically pleasing fragrances.

It is a further object of this invention to provide a method for removing sand utilizing cornstarch-based body powder.

The foregoing objects and other features and advantages of the present invention are achieved by a composition comprising a major amount of conventional starch, preferably cornstarch.

Other objects of this invention will be set forth in, or be apparent from, the following detailed description of the invention.

DETAILED DESCRIPTION OF THE INVENTION

The present invention relates to the use of body powder compositions containing from about 50–99% starch and from about 1–20% of baking soda, and may also contain other components normally utilized in such compositions.

Powder starches have been used for many years in dusting powder applications. While starches from various sources such as cornstarch, pregelatinized cornstarch, potato starch, sago starch, rice starch, tapioca starch and the like are commercially available, the most readily available form of starch for the desired use is cornstarch. Cornstarch is preferred since it has demonstrated skin affinity, uniform natural globular particle dimensionality and purity, as well as its ready availability. Most cornstarch normally produced for industrial, food and pharmaceutical uses is derived from field corn commonly known as yellow dent corn. This cornstarch consists of irregular angular white granules or fine powder of largely spherical to polygonal shaped particles. The particle size is such that not less than 99% passes through a 100 mesh screen and preferably at least 98% will pass through a 200 mesh screen. This cornstarch is utilized in an amount from about 80% to 99% by weight of the total composition, preferably from about 90% to 97.5% by weight of the total composition.

The pregelatinized cornstarch which is useful in the present invention is derived specifically from waxy maize corn. The pregelatinized cornstarch is cornstarch that has been chemically or mechanically processed to rupture all or part of the granules, preferably in the presence of water and subsequently dried. This pregelatinization of the cornstarch is achieved by well-known processing techniques in the starch industry. Generally, this process involves dispersing a cornstarch, preferably waxy maize cornstarch, into a dilute water slurry which is then doctored onto a drum drier internally heated by superheated steam. The surface temperature of the drum boils the slurry and simultaneously converts it to a pregelatinized form and also dries the boiled starch mixture into a film which is then stripped from the drum by a scraper blade. It has now been found that subsequently milling or grinding this film forms flaky particles of particle size such that at least 80%, and preferably about 98%, passes through a 200 mesh screen. These particles should have a bulk density of from about 3.0 gm./cubic in. to about 7.0 gm./cubic in. and a moisture content no greater than about 14% by weight and preferably no greater than about 7% by weight, to be suitable for use in the compositions of the present invention. The specific pregelatinized cornstarch is utilized in from about 1.0 to 20% by weight of the total composition, preferably from about 2.5 to 10%.

Baking soda, or sodium bicarbonate, is also added to the composition in an amount of about 1–20%. Baking soda functions to reduce the odor of the composition, adjust its pH, assist in the removal of the sand, and improve the texture of the composition.

Other components normally found in body powder compositions can be added if desired. Such components include flow agents such as tricalcium phosphate, dyes and colorings, bactericides, fungicides, medicaments and perfumes.

The perfumes or fragrances which are useful in the present invention include any commercial perfume which results in the fragrance desired by the formulator of the powder compositions. Commercial perfumes are a mixture of many components and these components all contribute to the particular fragrance which is characteristic of the mixture. In obtaining the desired fragrance, the ratio of components might be changed, some components may be added and some omitted. Examples of typical perfume components which can be formulated to make up a particular pleasing aroma include: lemon oil, musk ketone, ionoe, diphenyloxide, cedarwood, terpeneless, geranyl acetate, ylang ylang oil, cedryl acetate, isoeugenol, cinnamic alcohol, aurantheol, methyl anthranilate, vanillin, oil of bergamot, eugenol, oil of cananga, citral, tetrahydro linalool, oil patchouly, methyl icoeugenol, hexylcinnamic aldehyde, resin oil banum, resin balsam fir, musk aurbrette, nutmeg oil, methyl benzoate, palmarose oil, eucalyptus oil, orange oil, geranium oil, oil of lavender, jojoba and the like.

The perfume is utilized in an amount from about 0.01 to 1% by weight of the total composition, preferably from about 0.1 to 0.5% by weight of the total composition. If greater than about 1.0% by weight of perfume is utilized, the fragrance will usually be too strong initially and may deteriorate quickly. If less than 0.01% by weight of perfume is utilized, the fragrance will not be discernable to the user.

The compositions of the present invention can be prepared by well known mixing or blending procedures. For example, the cornstarch, baking soda and other ingredients, if utilized, are mixed and thoroughly blended and the perfume is then uniformly mixed therein. The resulting powder compositions exhibit excellent moisture absorbency and sand removal characteristics.

To remove sand, the powder is applied liberally to the affected area with one's hands. After light rubbing, the sand and powder are wiped off the body with the hands or a towel. Although not intending to be bound to one theory, it is believed that the composition absorbs water from either or both the surface of the sand particles and the skin which eliminates adherence of the sand to the skin.

Specific embodiments of the powder compositions prepared in accordance with the present invention are illustrated by the following representative examples. It will be understood, however, that the invention is not confined to the specific limitations set forth in the individual examples, but rather to the scope of the appended claims.

EXAMPLE 1

A body powder composition for removing sand is prepared as follows: 92.0 parts of conventional cornstarch and 7.65 parts of baking soda are thoroughly blended together by conventional means. 0.35 parts of fragrance are then added and the mixing is continued for about 5 minutes, followed by tumbling for about 15 minutes.

The resulting powder composition has the following formulation:

| Ingredient | % W/W |
|---|---|
| Cornstarch | 92.00 |
| Baking Soda | 7.65 |
| Fragrance | 0.35 |
| | 100.00 |

EXAMPLE 2

A body powder composition is prepared in accordance with the procedure of Example 1 having the following formulation:

| Ingredient | % W/W |
|---|---|
| Cornstarch | 98.10 |
| Tricalcium Phosphate | 1.50 |
| Fragrance | 0.40 |
| | 100.00 |

Various other features and embodiments of the present invention not specifically enumerated will be obvious to those skilled in the art, all of which may be achieved without departing from the spirit and the scope of the invention as defined by the following claims:

We claim:

1. A method for removing sand from a user's body comprising the steps of:

liberally applying a powder composition containing a major amount of cornstarch to an area of the body having sand adhered thereto;

rubbing said composition on said area; and wiping said composition and said sand off the area using one's hands or a towel or the like.

2. The method of claim 1 wherein said composition further comprises fragrance.

3. The method of claim 1 wherein said composition further comprises baking soda.

4. The method of claim 1 wherein said composition further comprises tricalcium phosphate.

5. A method for removing sand from a user's body comprising the steps of:

applying a powder composition containing cornstarch, baking soda and fragrance to an area of the body having sand adhered thereto;

rubbing said composition on said area; and wiping said composition and said sand off the area using one's hands or a towel or the like.

6. The method of claim 5 wherein said composition comprises about 92 parts of the cornstarch, about 7.65 parts of the baking soda and about 0.35 parts of the fragrance.

7. The method of claim 5 wherein said composition further comprises tricalcium phosphate.

8. A method for removing sand from a user's body comprising the steps of:

applying a powder composition containing approximately 98.10 parts cornstarch, approximately 1.50 parts tricalcium phosphate and 0.40 parts fragrance to an area of the body having sand adhered thereto;

rubbing said composition on said area; and wiping said composition and said sand off the area using one's hands or a towel or the like.

\* \* \* \* \*